(12) United States Patent
Jaime

(10) Patent No.: US 7,300,906 B2
(45) Date of Patent: Nov. 27, 2007

(54) CONTROL OF SULFHYDRYL COMPOUND ODOR IN ORGANOTHIOPHOSPHATE FORMULATIONS

(75) Inventor: Frank Jaime, Somerton, AZ (US)

(73) Assignee: Gowan Company, L.L.C., Yuma, AZ (US)

( * ) Notice: Subject to any disclaimer, the term of this patent is extended or adjusted under 35 U.S.C. 154(b) by 414 days.

(21) Appl. No.: 11/101,335

(22) Filed: Apr. 7, 2005

(65) Prior Publication Data

US 2006/0229204 A1    Oct. 12, 2006

(51) Int. Cl.
*A01N 57/20* (2006.01)
*A61L 9/00* (2006.01)

(52) U.S. Cl. .............. 504/203; 504/201; 504/365; 424/76.1; 424/76.2; 424/76.8

(58) Field of Classification Search ......... 504/203, 504/365
See application file for complete search history.

(56) References Cited

U.S. PATENT DOCUMENTS

| | | | |
|---|---|---|---|
| 2,759,010 A | 8/1956 | Lorenz et al. | |
| 2,767,194 A | 10/1956 | Fancher | |
| 2,988,474 A | 6/1961 | Szabo et al. | |
| 3,642,960 A | 2/1972 | Pitt et al. | |
| 4,368,133 A * | 1/1983 | Forsberg | 252/75 |
| 4,370,301 A | 1/1983 | Doi et al. | |
| 4,419,252 A * | 12/1983 | Shim | 508/373 |
| 4,752,604 A | 6/1988 | Chavdarian et al. | |
| 6,369,001 B1 * | 4/2002 | Jimoh | 504/118 |
| 6,713,433 B2 * | 3/2004 | Jimoh | 504/127 |

* cited by examiner

*Primary Examiner*—John Pak
(74) *Attorney, Agent, or Firm*—Quarles & Brady LLP; Gavin J. Milczarek-Desai

(57) ABSTRACT

Sulfhydryl odors in organothiophosphate formulations are suppressed by treatment of the thiophosphate compound (e.g., bensulide) during preparation of the formulation with a selected emulsifier agent, ethoxylated tallow amine. The amine and any reacting products resulting from the treatment are retained in the final formulation. The amine will continue to react with the mercaptan and other sulfhydryl compounds formed by the continuing degradation of the thiophosphate compound, thereby providing further odor control.

21 Claims, 1 Drawing Sheet

CONTROL OF SULFHYDRYL COMPOUND ODOR IN ORGANOTHIOPHOSPHATE FORMULATIONS

BACKGROUND OF THE INVENTION

1. Field of the Invention

The present invention concerns thiophosphate-containing biocide preparations, and, more particularly, agricultural formulations of biocidal thiophosphate that have a reduced tendency to emit sulfurous vapors.

2. Description of the Related Art

Organothiophosphate compounds refer generally to those containing carbon-phosphorus bonds in which the phosphorus component is also bonded to one or more sulfur atoms. Many of these compounds function as pesticides. Hence, Organothiophosphate insecticides are well known and widely used for crop protection. Included among these compounds are, for example, the commercially available preparations of bensulide known under the trademarks Bensumec™, Betamec™, Betasan™, Disan™, Exporsan™, Prefar™, Pre-San™, and others.

Unfortunately, the organothiophosphate-type insecticides typically contain sulfhydryl compounds, such as thiols or mercaptans, that produce a well known and irritating sulfurous (i.e., "rotten egg") odor. The presence of compounds such as mercaptans in formulations of these insecticides is due to a number of factors. In some instances, thiophosphate analogs of the organothiophosphate compound are present as by-products of the synthesis, with these analog species tending to decompose to mercaptans. Moreover, organothiophosphate compounds tend to degrade or decompose over time to produce mercaptans, particularly when subjected to heating. Regardless of how the sulfhydryl odor is produced, it is detrimental from an environment point of view, as well as from handling and field application perspectives.

Bensulide technical (S—(O, O-diisopropyl phosphorodithioate) ester of N-(2-mercaptoethyl) benzenesulfonamide) is the active ingredient in several organothiophosphate pesticide formulations. Bensulide technical is synthesized at a purity range from 92.0% to 95.0%. The remaining 6% percent are process impurities, with some of these impurities being mercaptans and sulfides produced from the reaction of the dithiophosphoric acid.

Bensulide is not considered to be a very stable compound. Indeed, bensulide undergoes an autocatalytic decomposition such that, after 10-20% of the material has decomposed, a large increase in decomposition rate occurs. Decomposition products are known to be mercaptans and sulfides.

Impurities in bensulide have been purged and trapped for analysis by gas chromatography/mass spectrometry (for example, see Bobbi Kahn, Analysis & Certification of Product Ingredients in Betasan, Stauffer Chemical Company, Richmond Research Center (RCC-9/2/86 86-88). The largest impurity was identified as hydrogen sulfide ($H_2S$) and was the only impurity in the headspace analysis that was not found in the actual bensulide composite sample.

Although there are a number a ways known in the art to control various chemical odors, there are often unknown or unwanted chemical changes or other side effects that occur. Moreover, many methods are time consuming, involve hazardous materials, and are relatively expensive to carry out on commercially useful scales, especially when filtration/separation and disposal costs are considered. Thus, there remains a need in the art for new and improved ways for controlling odor in organothiophosphate formulations.

SUMMARY OF THE INVENTION

The invention generally relates to compositions and methods involving the control of sulfhydryl (e.g., mercaptan) odors in thiophosphate biocide formulations. The odors are suppressed by treatment of thiophosphate compounds (such as bensulide) during preparation of the formulation with a selected emulsifier agent, an ethoxylated amine, yielding a chemically and physically stable biocidal formulation with substantially low sulfhydryl odor.

Acting as a scavenger, the ethoxylated amine will continue to react with the mercaptan-forming compounds from the continuing degradation of the thiophosphate compound, thereby achieving a formulation with substantially low odor. Preferably, ethoxylated tallow amine is used as the scavenger.

Various other purposes and advantages of the invention will become clear from its description in the specification that follows. Therefore, to the accomplishment of the objectives described above, this invention includes the features hereinafter fully described in the detailed description of the preferred embodiments, and particularly pointed out in the claims. However, such description discloses only some of the various ways in which the invention may be practiced.

DETAILED DESCRIPTION OF THE PREFERRED EMBODIMENTS

Figure 1:
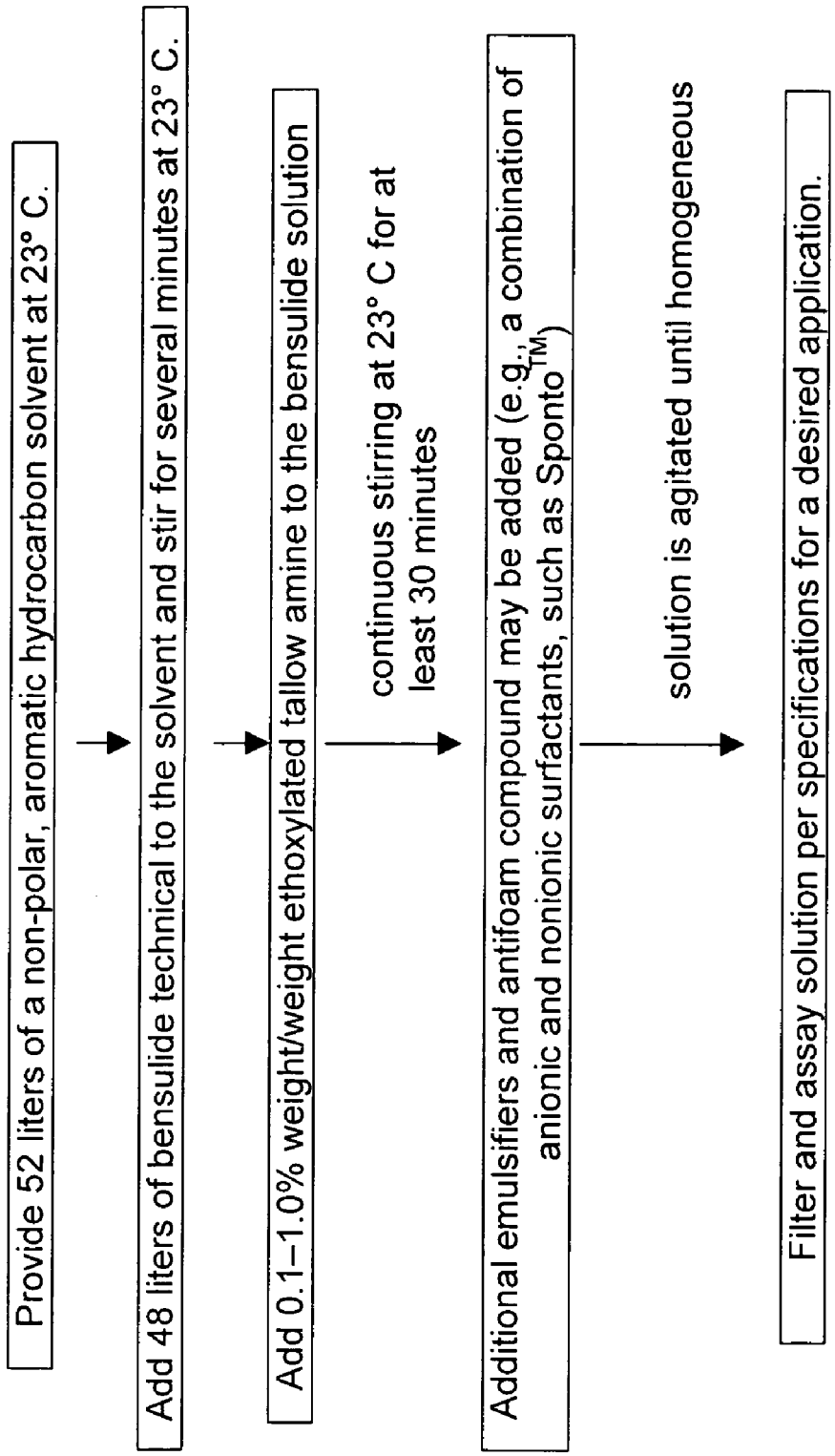
FIG. 1 is a flowchart outlining the steps of a particularly preferred method of the invention.

The invention relates generally to compositions and processes that involve substantially suppressing the sulfhydryl odors associated with organothiolphosphate formulations by using effective amounts of an ethoxylated amine, such as ethoxylated tallow amine.

The terms "substantially reduced or suppressed odor" or "substantially low odor" are used in the description in a qualitative and quantitative sense. Qualitatively, "substantially reduced or suppressed odor" or "substantially low odor" indicate a substance that is deemed acceptable to a human user due to the presence of little if any odor. Quantitatively, a "substantially reduced or suppressed odor" or "substantially low odor" composition of the invention contains very minute amounts of sulfhydryl compounds as analyzed by a Draeger pump, i.e., the detection of 0.5 parts per million (PPM) or fewer of hydrogen sulfide-containing compounds.

As used herein, the term "alkyl" is meant to designate straight or branched, saturated alkyl groups of from 1 to 4 carbon atoms.

In one embodiment of the invention, a organothiophosphate formulation is rendered substantially low odor through being contacted with a solution of an ethoxylated tallow amine as describing in the following non-limiting example illustrated in FIG. 1:

A batch of fifty-two liters of non-polar solvent is prepared at 23° C. (any aromatic hydrocarbon, e.g., A100, A150, A200) and stirred. Forty-eight liters bensulide technical is added and stirred for several minutes at 23° C. Next, 0.1-1.0% (weight/weight) ethoxylated tallow amine is added to the one hundred liters of bensulide technical/non-polar solvent solution, with continuous stirring at 23° C. for at least 30 minutes.

In this particular embodiment, additional emulsifiers and antifoam compound are provided (e.g., a combination of anionic and nonionic surfactants such as Sponto™) in a recommended amount per the manufacturer, and the solution is agitated until homogeneous. Lastly, the solution is filtered and assayed per specifications for a desired application.

In another embodiment of the invention, porous granules Attapulgite (Attasorb RVM LVM) containing adsorbed ethoxylated tallow amine are contacted with an organothiophosphate solution in the amount of 0.1-1.0% by mass under the same temperature and time conditions as used above.

In other embodiments of the invention, non-solvated (neat) or solid ethoxylated amine is used in lieu of a solution. Moreover, other ethoxylated amines are contemplated for use in the invention, such as ethoxylated coconut amines, ethoxylated alkyl propylene amines, and mixtures thereof.

The inventor performed experiments to compare several methods for controlling sulfhydryl odors to the method of the invention. These processes included: treatment with activated carbon (an adsorptive reaction), treatment with cumene hydroperoxide (an oxidation chemical reaction), and treatment with ethanolamine or ethoxylated tallow amines (a neutralization chemical reaction). The amount of compounds added, or reacted in the formulation, ranged form 0.1-1.0% by weight. This amount is insufficient to react with the active ingredient of the test organothiolphosphate S—(O, O-diisopropyl phosphorodithioate) ester of N-(2-mercaptoethyl) benzenesulfonamide (bensulide, sold under the trademark Prefar™ 4E).

Activated Carbon Adsorption Process

Adsorption is the term for the enrichment of gaseous or dissolved substances (the adsorbate) on the boundary surface of a solid (the adsorbent). From a chemist's perspective, activated carbon is an imperfect form of graphite. This imperfect structure results in a higher degree of porosity and more than a million-fold range of pore sizes, from visible cracks and crevices to gaps and voids of molecular dimensions. Intermolecular attractions in the smallest pores result in adsorption forces.

The adsorption process generally is of an exothermal nature. With increasing temperature and decreasing adsorbate concentrations, the adsorption capacity decreases. Moreover, the mercaptans and other sulfides will, even in an adsorbed state, oxidize on the activated carbon due to the presence of oxygen.

In terms of economics, activated carbon has a procurement cost of about $0.95 per pound and a disposal cost of about $1.00 per pound. Laboratory tests indicate that 5 lbs. of activated carbon will reduce the odor of about a gallon of Prefar™ 4E. This cost estimate does not include the filtration equipment needed at an estimated cost of $15,000. Thus, treatment with activated carbon is relatively expensive to use in industrial production quantities.

In terms of chemical and physical characteristics, treatment with activated carbon apparently does not alter (versus untreated) the flashpoint, cold stability, physical stability, or chemical stability of Prefar™ 4E. However, decomposition of bensulide into malodorous compounds was detected as the test formulation aged in glass. Thus, while the activated carbon removes the sulfhydryl compounds during the initial treatment process, the malodorous compounds are regenerated as would be expected during aging.

Cumene Hydroperoxide Treatment Process

The chemical reactions of interest that take place in the presence of cumene hydroperoxide essentially involve the oxidization of mercaptans to disulfides.

In terms of cost, the market for phenol generally dictates what happens to cumene. Aside from bisphenol-A, phenol's other major end uses (i.e., phenolic resins for adhesives and caprolactam for nylon) are tied to cyclic housing and construction outlets. Historic price information (1981-1996) includes a price range from a high of 30.5 cents per pound to a low of 15 cents per pound.

Hence, it is estimated that cumene hydroperoxide treatment of a gallon of Prefar 4E will cost in the vicinity of 32 cents. However, the filtration, environmental registration approval, and disposal costs (as mentioned above, hydroperoxide has hazardous characteristics) associated with this method are likely to increase the per gallon cost.

In terms of chemical and physical characteristics, treatment with cumene hydroperoxide apparently does not alter (versus untreated) the flashpoint, cold stability, physical stability, or chemical stability of Prefar™ 4E. However, the long-term use of hydroperoxide compounds for odor control is problematic as these compounds have been found to be explosive and to require special handling.

Ethanolamine Treatment Process

Ethanolamines are used in production of monoalkanolamides, for nonionic detergents, emulsifiers and soaps, in dry cleaning, in wool treatment, in fuel oil additives, in water-in-oil emulsifiers, as a corrosion inhibitor in pharmaceuticals, as a dispersing agent for agricultural chemical, and widely used in the cosmetic industry.

Historic price information for ethanolamine (1981-1996) includes a range from a high of 65 cents per pound to a low of 42.5 cents per pound. Currently, there appears to be strong demand for ethanolamine such that the estimated cost for the treatment of a gallon of Prefar 4E will cost in the vicinity of 67 cents. However, this estimate does not include any filtration or disposal costs associated with this method. Therefore, the per gallon cost is likely to be on par with, or greater than, the other treatment methods tested.

In terms of chemical and physical characteristics, treatment with ethanolamine apparently does not alter (versus untreated) the flashpoint, cold stability, physical stability, or chemical stability of Prefar™ 4E. However, the long-term efficacy of odor control with ethanolamine has been rendered difficult to study and utilize due to the possible removal of ethanolamine from the EPA's list of inert pesticides. Moreover, plant phytotoxicity characteristics still need to be tested Ethoxylated Tallow Amine Treatment Process Ethoxylated tallow amine is widely used in the agricultural industry as an emulsifier. Emulsifiers are surface active molecules (surfactants) that lie at the interface of water and substances that do not readily mix with water, such as oil. Each molecule of an emulsifier contains a hydrophilic (water loving) portion and a lypophilic (oil loving) portion. In agricultural preparations, this "dualistic property" of emulsifiers are used to form an emulsion, which is a dispersion of one insoluble liquid into another, in order to maintain a mixed state during spraying and upon contact with a plant.

The chemical behavior of mercaptans and sulfides contrasts with that of alcohol and ethers in some important ways. Since hydrogen sulfide is a much stronger acid than water (by more than ten million fold), one expects, and finds, mercaptans and sulfides to be stronger acids than equivalent alcohols an phenols. When primary, secondary, and tertiary amines react with acids, they form aminium salts.

Although the basicity of ethers is roughly a hundred times greater than that of the equivalent sulfides, the nucleophilicity of sulfur is much greater than that of oxygen, leading to a number of interesting and useful electrophilic substitutions of sulfur that are not normally observed by oxygen. Sulfides, for example, react with alkyl halides to give ternary sulfonium salts, in the same manner that tertiary amines are alkylated to quaternary ammonium salts. Primary, secondary, and tertiary amines can also be alkylated. In this manner, ethoxylated tallow amines provide a "target" for the sulfhydryl compounds present in organothiolphosphate formulations.

In terms of cost, ethoxylated tallow amine is basically an animal fat that is ethoxylated to make surfactants found in soaps, detergents, shampoos, and the like. Moreover, polyethoxylated tallow amine (POEA) is a nonionic surfactant used worldwide for many commercial biocide formulations.

It is estimated that ethoxylated tallow amine treatment of a gallon of Prefar 4E will cost in the vicinity of $1.14. However, there are no filtration or disposal costs associated with this method because the ethoxylated tallow amine remains an active component within the organothiophosphate formulation.

In other words, the ethoxylated tallow amine will act as a "scavenger" by continuing to react with the mercaptan-forming compounds from the degradation of the thiophosphate compound, thereby keeping the formulation substantially low odor for at least four months under test conditions. Since test conditions utilized elevated temperatures, the equivalent storage time under warehouse conditions is thought to be on the order of two years. Thus, odor control was found to be maintained well over commercially relevant periods of time.

In terms of chemical and physical characteristics, treatment with ethoxylated tallow amine apparently does not alter (versus untreated) the flashpoint, cold stability, physical stability, or chemical stability of Prefar™ 4E. While it should be noted that the pH of bensulide that has undergone ethoxylated tallow amine process is 8.28, whereas the pH of the untreated formulation is 6.15, this change is irrelevant to bensulide's stability. Bensulide is relatively stable in acidic and alkali conditions, i.e. it has a DT50>200 days (pH 5-9, 25° C.).

Importantly, very little decomposition of bensulide into malodorous compounds was detected as the test formulation aged in glass for four months at 50° C., which is the equivalent of over 2 years under typical warehouse storage conditions. Moreover, because ethoxylated tallow amine is a commonly used emulsifier and listed in the EPA approved list of inert pesticides, handling, storage, and disposal present no special hazards.

Summary of Test Results

In comparing the four test treatments above, the activated carbon adsorption method is the most straight forward from a regulatory perspective (i.e., it does not require any submissions to EPA). However, it also is the most expensive way of deriving a reduced odor formulation due to the disposing and operating cost of the activated carbon. The cumene hyderperxide process would be useful if one could overcome its hazardous characteristics. The ethanolamine process is promising, but there are obstacles, such as possible removal from EPA's approved list of inerts.

In contrast, the ethoxylated tallow amine process would overcome all obstacles involved. Advantageously, ethoxylated amines (and particularly ethoxylated tallow amine) would be a replacement for another emulsifying agent, thereby simplifying and making more economical the formulation of a biocidal solution that is also substantially low odor. Also, ethoxylated amines may be used as an additional emulsifying agent that can further improve dilution and application properties and that can provide continuing control of sulfhydryl odor without affecting the chemical properties of organothiophosphate formulations. Moreover, the cost of the ethoxylated amine process does not deviate much from the existing formulation cost.

Various changes in the details and components that have been described may be made by those skilled in the art within the principles and scope of the invention herein described in the specification and defined in the appended claims. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent processes and products. All references cited in this application are hereby incorporated by reference herein.

What is claimed is:

1. A process for the preparation of a bensulide composition with reduced sulfhydryl compound odor, comprising the step of contacting a formulation of bensulide with an effective sulfhydryl compound odor reducing amount of an ethoxylated amine selected from the group consisting of ethoxylated tallow amine, ethoxylated coconut amine, ethoxylated alkyl propylene amine, polyethoxylated amine, and mixtures thereof.

2. The process of claim 1, wherein said ethoxylated amine is ethoxylated tallow amine.

3. The process of claim 1, wherein said effective sulfhydryl compound odor reducing amount of an ethoxylated amine comprises 0.1-1.0% by weight.

4. The process of claim 2, wherein said effective sulfhydryl compound odor reducing amount of an ethoxylated amine comprises 0.1-1.0% by weight of said ethoxylated tallow amine.

5. The process of claim 1, wherein said formulation of bensulide is contacted with a solution of said ethoxylated amine in the presence of a non-polar solvent.

6. The process of claim 1, wherein said ethoxylated amine is the sole emulsifying agent in the bensulide composition.

7. The process of claim 1, wherein said ethoxylated amine is combined with at least one other emulsifying agent.

8. The process of claim 1, wherein said ethoxylated amine is disposed upon porous granules and contacted with said formulation of bensulide.

9. The process of claim 2, wherein said ethoxylated tallow amine is disposed upon porous granules and contacted with said formulation of bensulide.

10. A composition of matter, comprising: a bensulide formulation that contains an effective sulfhydryl compound odor reducing amount of an ethoxylated amine selected from the group consisting of ethoxylated tallow amine, ethoxylated coconut amine, ethoxylated alkyl propylene amine, polyethoxylated amine, and mixtures thereof.

11. The composition of claim 10, wherein the composition has a sulfhydryl compound contaminant level of 0.5 parts per million or less.

12. The composition of claim 10, wherein said ethoxylated amine is ethoxylated tallow amine.

13. The composition of claim 10, wherein said effective sulfhydryl compound odor reducing amount of an ethoxylated amine comprises 0.1-1.0% by weight.

14. The composition of claim 12, wherein said effective sulfhydryl compound odor reducing amount of an ethoxylated amine comprises 0.1-1.0% by weight of said ethoxylated tallow amine.

15. The composition of claim 10, wherein said bensulide formulation further comprises a non-polar solvent.

16. The composition of claim 10, wherein said bensulide formulation further comprises an antifoaming compound.

17. The composition of claim 10, wherein said ethoxylated amine is the sole emulsifying agent in the bensulide formulation.

18. The composition of claim 10, wherein a stored solution of said bensulide formulation containing an effective sulfhydryl compound odor reducing amount of said ethoxylated amine retains a sulfhydryl compound contaminant level of 0.5 parts per million or fewer for at least four months at 50° C.

19. The composition of claim 12, wherein a stored solution of said bensulide formulation containing an effective sulfhydryl compound odor reducing amount of said ethoxylated tallow amine retains a sulfhydryl compound contaminant level of 0.5 parts per million or fewer for at least four months at 50° C.

20. A method for preparing a composition of bensulide low in mercaptan-form contaminants, said method comprising the steps of:
    (a) mixing solutions comprising bensulide and a non-polar solvent; and
    (b) contacting said solutions of step (a) with an effective mercaptan-form contaminant reducing amount of an emulsifier agent comprising an ethoxylated amine selected from the group consisting of ethoxylated tallow amine, ethoxylated coconut amine, ethoxylated alkyl propylene amine, polyethoxylated amine, and mixtures thereof.

21. The method of claim 20, wherein said ethoxylated amine is ethoxylated tallow amine.

\* \* \* \* \*